(12) United States Patent
Pikus et al.

(10) Patent No.: US 9,398,900 B2
(45) Date of Patent: Jul. 26, 2016

(54) DEVICE AND METHOD FOR TREATING VARICOSE VEINS

(75) Inventors: Valery Pikus, Ashdod (IL); Boris Gliner, Rechovot (IL)

(73) Assignee: SIMEDEQ Medical Equipment Ltd., Ashdod (IL)

( * ) Notice: Subject to any disclaimer, the term of this patent is extended or adjusted under 35 U.S.C. 154(b) by 0 days.

(21) Appl. No.: 13/337,337

(22) Filed: Dec. 27, 2011

(65) Prior Publication Data

US 2012/0172902 A1    Jul. 5, 2012

Related U.S. Application Data

(62) Division of application No. 11/579,927, filed as application No. PCT/IL2005/000494 on May 10, 2005, now Pat. No. 8,109,952.

(30) Foreign Application Priority Data

May 11, 2004  (IL) .......................................... 161928

(51) Int. Cl.
  *A61B 17/22*  (2006.01)
  *A61B 17/00*  (2006.01)
  *A61B 17/04*  (2006.01)

(52) U.S. Cl.
  CPC . *A61B 17/00008* (2013.01); *A61B 2017/00336* (2013.01); *A61B 2017/00349* (2013.01); *A61B 2017/00398* (2013.01); *A61B 2017/00734* (2013.01); *A61B 2017/0412* (2013.01); *A61B 2017/0432* (2013.01)

(58) Field of Classification Search
  CPC ................. A61B 17/00008; A61B 2017/0432; A61B 2017/0412; A61B 2017/00349; A61B 2017/00336; A61B 2017/00398; A61B 2017/00734
  USPC .......................................... 606/159; 433/102
  See application file for complete search history.

(56) References Cited

U.S. PATENT DOCUMENTS

| 3,635,223 | A | * | 1/1972 | Klieman ....................... 606/194 |
| 4,723,546 | A | | 2/1988 | Zagorski |
| 5,011,489 | A | * | 4/1991 | Salem .......................... 606/159 |
| 5,792,168 | A | * | 8/1998 | Suval ............................ 606/185 |
| 5,893,858 | A | * | 4/1999 | Spitz ............................ 606/170 |
| 6,022,313 | A | * | 2/2000 | Ginn et al. .................... 600/114 |

(Continued)

FOREIGN PATENT DOCUMENTS

| DE | 3728260 | | 4/1988 |
| DE | 19809816 | * | 3/1998 |

(Continued)

OTHER PUBLICATIONS

International Preliminary Report on Patentability Dated Nov. 23, 2006 From the International Bureau of WIPO Re.: Application No. PCT/IL2005/000494.

(Continued)

*Primary Examiner* — Julie A Szpira

(57) ABSTRACT

A surgical instrument for treatment of superficial varicose veins in a body is provided. The surgical instrument includes at least one vein-engaging element disposed within or on a housing being adapted for insertion into a tissue. The at least one vein-engaging element is operable to a vein-engaging state whereby it protrudes from the housing at a length thereof.

16 Claims, 12 Drawing Sheets

(56) References Cited

U.S. PATENT DOCUMENTS

| | | | |
|---|---|---|---|
| 6,431,863 B1* | 8/2002 | Sachdeva et al. | 433/102 |
| 6,660,016 B2* | 12/2003 | Lindsay | 606/159 |
| 6,767,339 B2* | 7/2004 | Reydel | 604/175 |
| 8,109,952 B2 | 2/2012 | Pikus et al. | |
| 2003/0125759 A1* | 7/2003 | Mirizzi et al. | 606/159 |
| 2003/0211442 A1* | 11/2003 | Abel | 433/102 |
| 2004/0087967 A1* | 5/2004 | Schur et al. | 606/108 |
| 2004/0260317 A1* | 12/2004 | Bloom et al. | 606/151 |
| 2005/0216048 A1 | 9/2005 | Suval et al. | |
| 2007/0270893 A1 | 11/2007 | Pikus et al. | |
| 2010/0030247 A1* | 2/2010 | Pikus et al. | 606/159 |
| 2011/0124958 A1* | 5/2011 | Nelson | 600/36 |

FOREIGN PATENT DOCUMENTS

| | | | |
|---|---|---|---|
| DE | 19809816 | | 9/1998 |
| DE | 19754781 | | 6/1999 |
| JP | 08-507714 | | 8/1996 |
| SU | 944568 | | 7/1982 |
| SU | 1371689 | | 2/1988 |
| SU | 1554900 | | 4/1990 |
| SU | 1556667 | | 4/1990 |
| WO | WO9421177 | * | 3/1994 |
| WO | WO 94/21177 | | 9/1994 |
| WO | WO 2005/107371 | | 11/2005 |
| WO | WO 2008/093337 | | 8/2008 |

OTHER PUBLICATIONS

International Search Report and the Written Opinion Dated May 31, 2006 From the International Searching Authority Re.: Application No. PCT/IL05/00494.
Office Action Dated Nov. 20, 2006 From the Israeli Patent Office Re.: Application No. 179157.
Official Action Dated Dec. 17, 2008 From the Patent Office of the Russian Federation Re.: Application No. 2006143637/14 and Its Translation Into English.
Communication Pursuant to Article 9493) EPC Dated Oct. 27, 2010 From the European Patent Office Re. Application No. 05740366.9.
Examiner's Report Dated Apr. 1, 2010 From the Australian Government, IP Australia Re. Application No. 2005239907.
Examiner's Report Dated May 30, 2011 From the Australian Government, IP Australia Re. Application No. 2005239907.
International Preliminary Report on Patentability Dated Jan. 21, 2010 From the International Bureau of WIPO Re.: Application No. PCT/IL2008/000129.
International Search Report Dated Jul. 16, 2008 From the International Searching Authority Re.: Application No. PCT/IL2008/000129.
International Search Report Dated May 31, 2006 From the International Searching Authority Re.: Application No. PCT/IL2005/000494.
Notice of Allowance Dated Oct. 3, 2011 From the US Patent and Trademark Office Re.: U.S. Appl. No. 11/579,927.
Office Action Dated Oct. 27, 2009 From the Israel Patent Office Re.: Application No. 179157 and Its Translation Into English.
Official Action Dated Mar. 4, 2009 From the US Patent and Trademark Office Re.: U.S. Appl. No. 11/579,927.
Official Action Dated Dec. 8, 2009 From the US Patent and Trademark Office Re.: U.S. Appl. No. 11/579,927.
Official Action Dated Dec. 17, 2008 From the Patent Office of the Russian Federation Re.: Application No. 2006143637 and Its Translation Into English.
Official Action Dated Sep. 21, 2011 From the US Patent and Trademark Office Re. U.S. Appl. No. 12/525,091.
Official Action Dated May 25, 2010 From the US Patent and Trademark Office Re.: U.S. Appl. No. 11/579,927.
Official Action Dated Oct. 29, 2008 From the US Patent Office Re.: U.S. Appl. No. 11/579,927.
Response Dated Feb. 8, 2010 to Official Action of Dec. 8, 2009 From the US Patent and Trademark Office Re.: U.S. Appl. No. 11/579,927.
Response Dated Nov. 24, 2010 to Official Action of May 25, 2010 From the US Patent and Trademark Office Re.: U.S. Appl. No. 11/579,927.
Response Dated Aug. 25, 2011 to Notice of Reason for Rejection of Apr. 8, 2011 From the Japanese Patent Office Re. Application No. 2007-512719.
Response Dated Feb. 27, 2011 to Communication Pursuant to Article 9493) EPC of Oct. 27, 2010 From the European Patent Office Re. Application No. 05740366.9.
Response Dated Mar. 28, 2011 to Examiner's Report of Apr. 1, 2010 From the Australian Government, IP Australia Re. Application No. 2005239907.
Response Dated Jun. 30, 2011 to Examiner's Report of May 30, 2011 From the Australian Government, IP Australia Re. Application No. 2005239907.
Supplementary European Search Report Dated Jul. 1, 2010 From the European Patent Office Re. Application No. 05740366.9.
Translation of Notice of Reason for Rejection Dated Apr. 8, 2011 From the Japanese Patent Office Re. Application No. 2007-512719.
Translation of the Patent Search Report Dated Aug. 4, 2005 From the Eurasian Patent Organization, The Eurasian Patent Office Re.: Application No. 200500477.
Written Opinion Dated Jul. 16, 2008 From the International Searching Authority Re.: Application No. PCT/IL2008/000129.
Written Opinion Dated May 31, 2006 From the International Searching Authority Re.: Application No. PCT/IL2005/000494.
Resposne Dated Dec. 21, 2011 to Official Action of Sep. 21, 2011 From the US Patent and Trademark Office Re. U.S. Appl. No. 12/525,091.
Translation of Official Decision of Rejection Dated Jan. 17, 2012 From the Japanese Patent Office Re. Application No. 2007-512719.
Requisition by the Examiner Dated May 1, 2012 From the Canadian Intellectual Property Office Re. Application No. 2,566,490.
Office Action Dated Nov. 15, 2012 From the Israel Patent Office Re.: Application No. 179157 and Its Translation Into English.
Official Action Dated Mar. 24, 2014 From the US Patent and Trademark Office Re. U.S. Appl. No. 12/525,091.
Supplementary European Search Report and the European Search Opinion Dated Feb. 18, 2015 From the European Patent Office Re. Application No. 08702709.0.
Communication Pursuant to Article 94(3) EPC Dated Dec. 22, 2014 From the European Patent Office Re. Application No. 05740366.9.

* cited by examiner

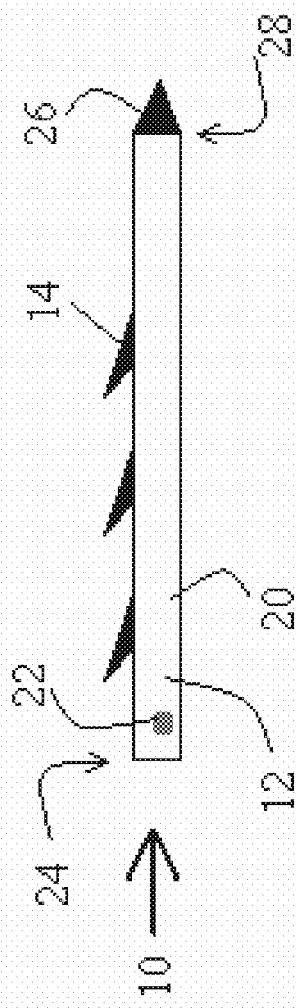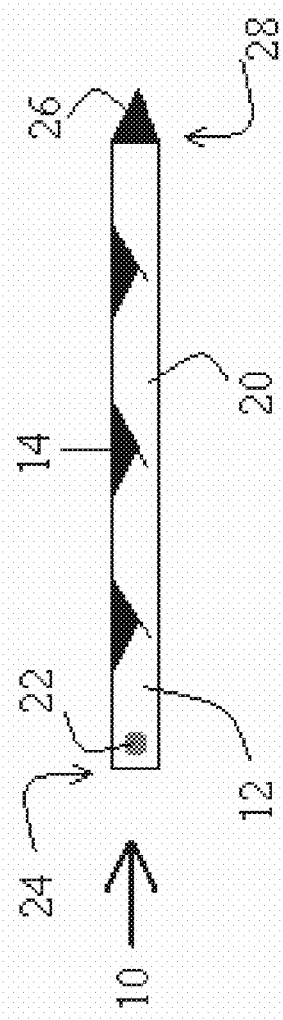

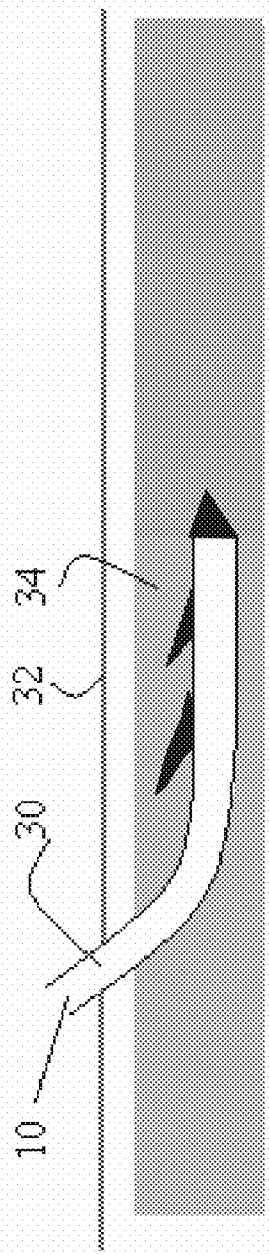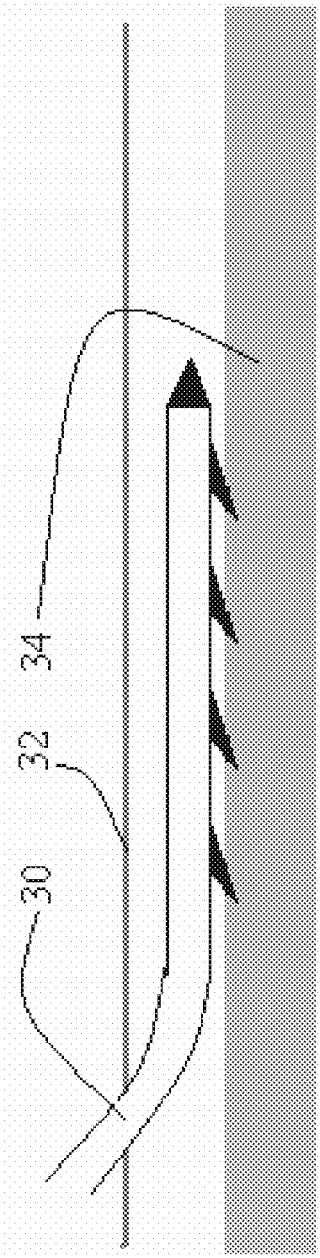

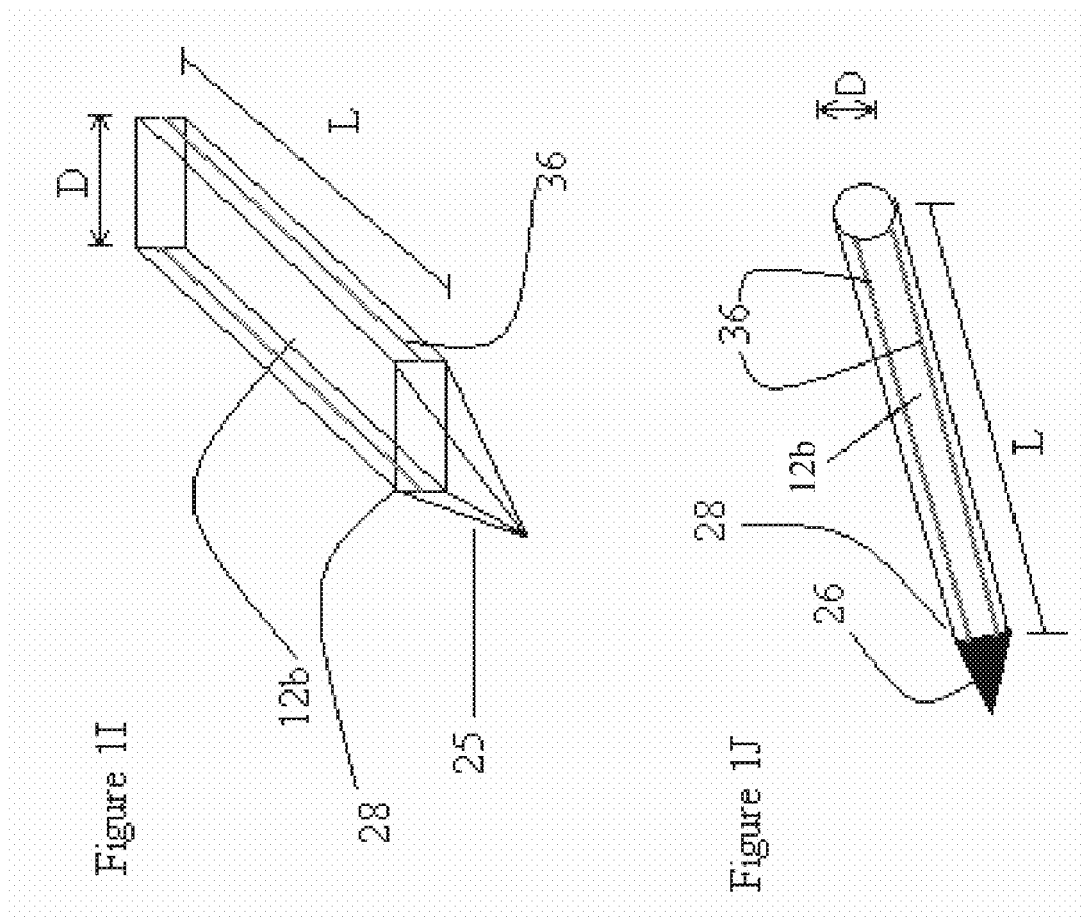

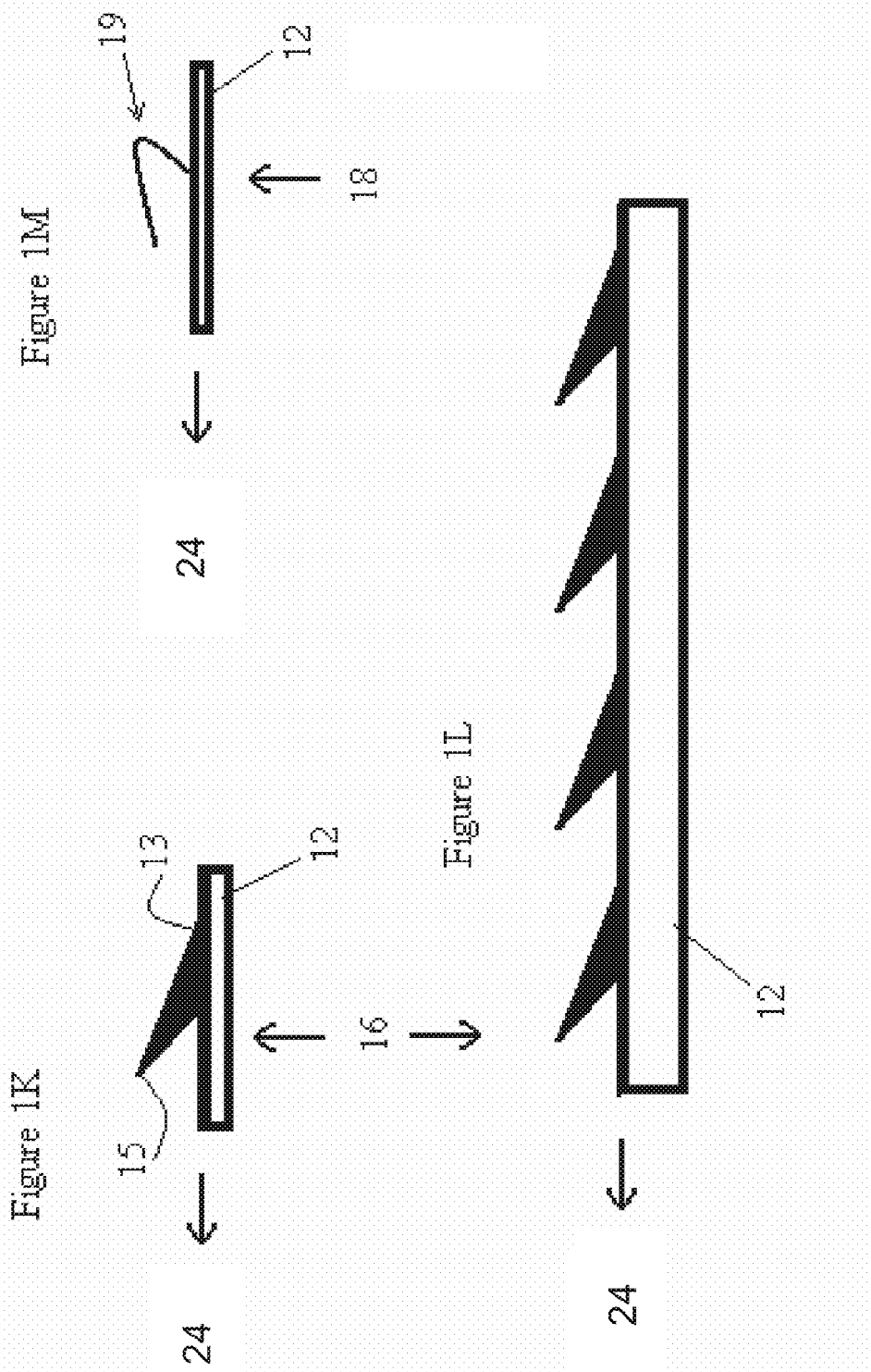

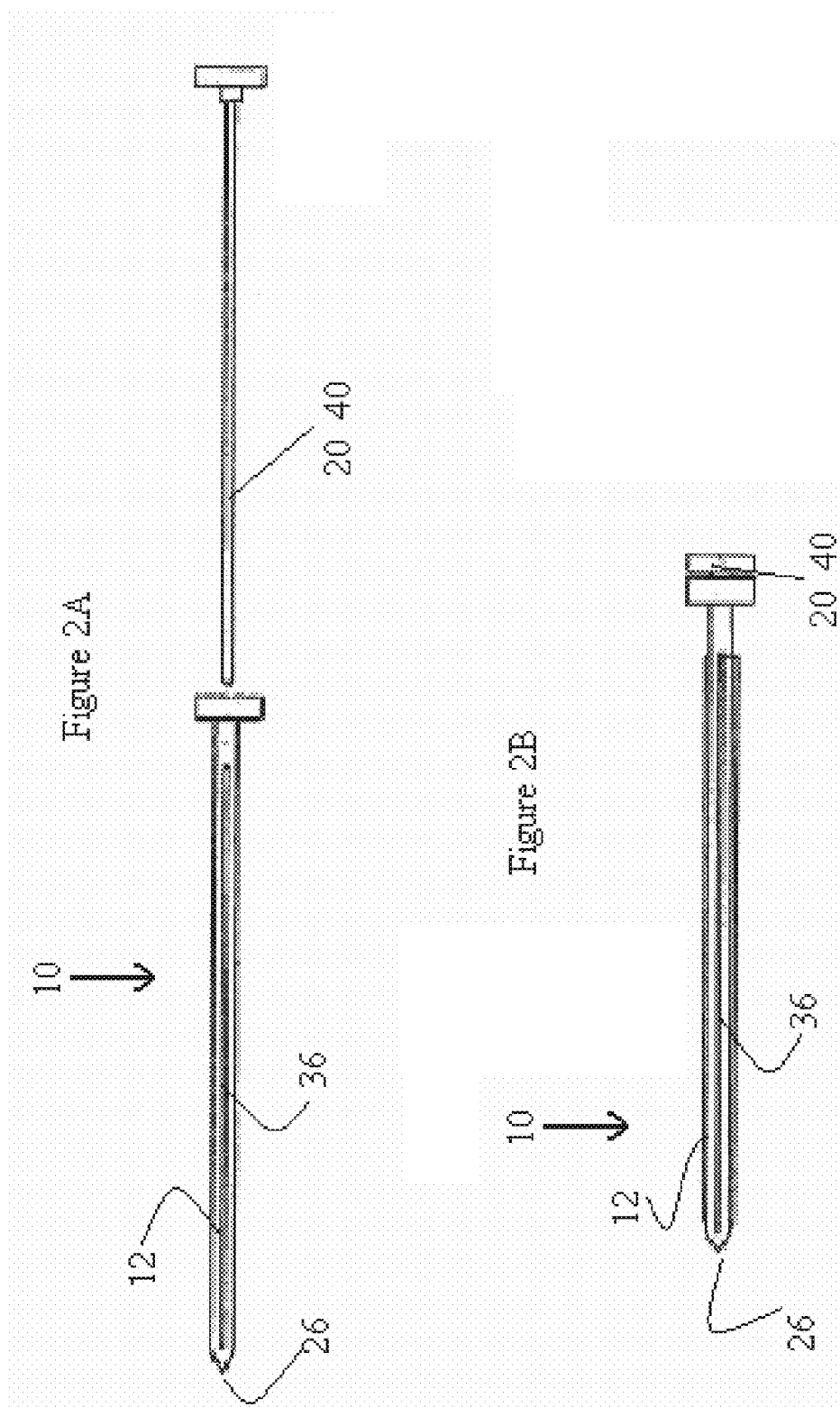

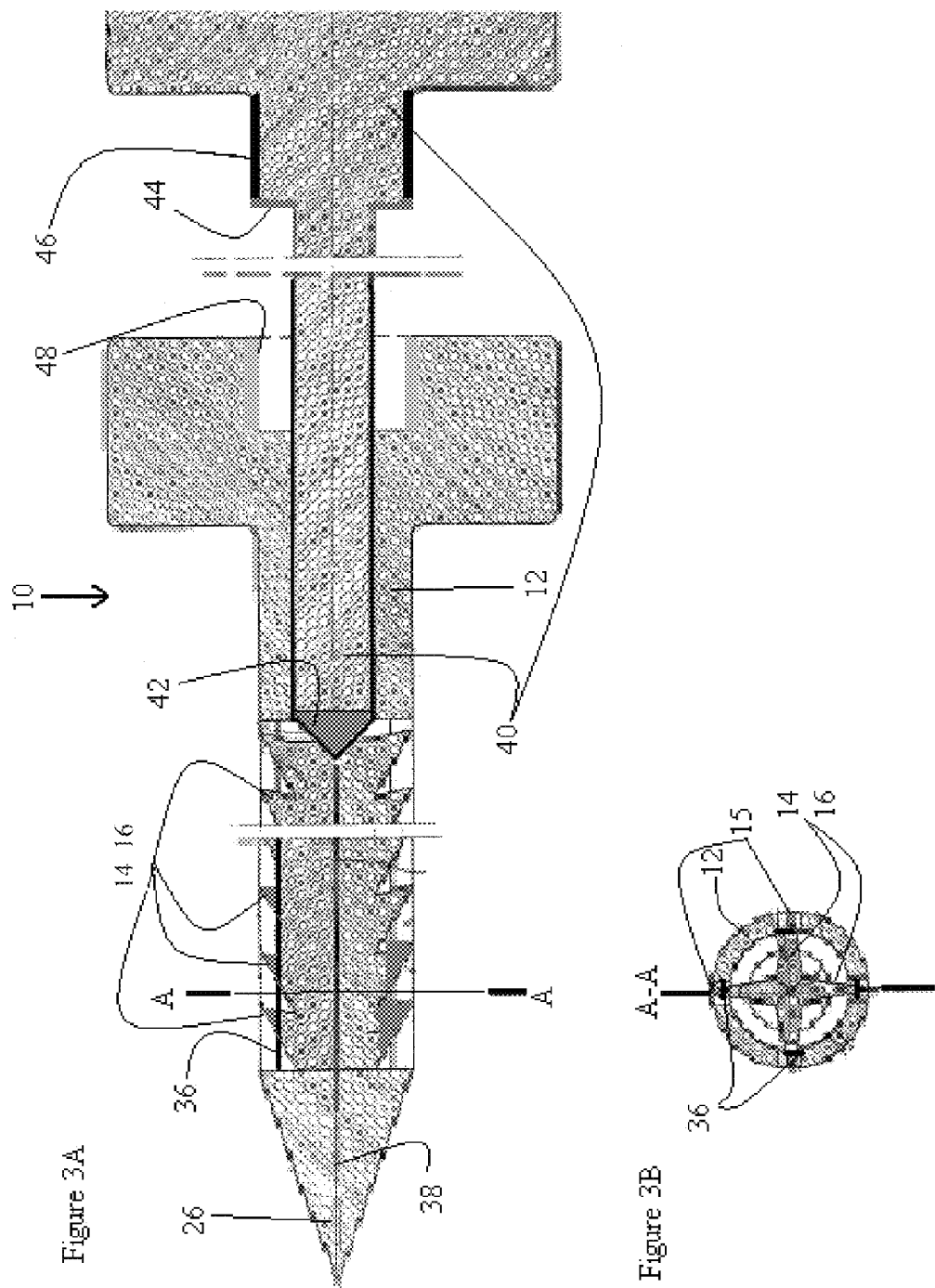

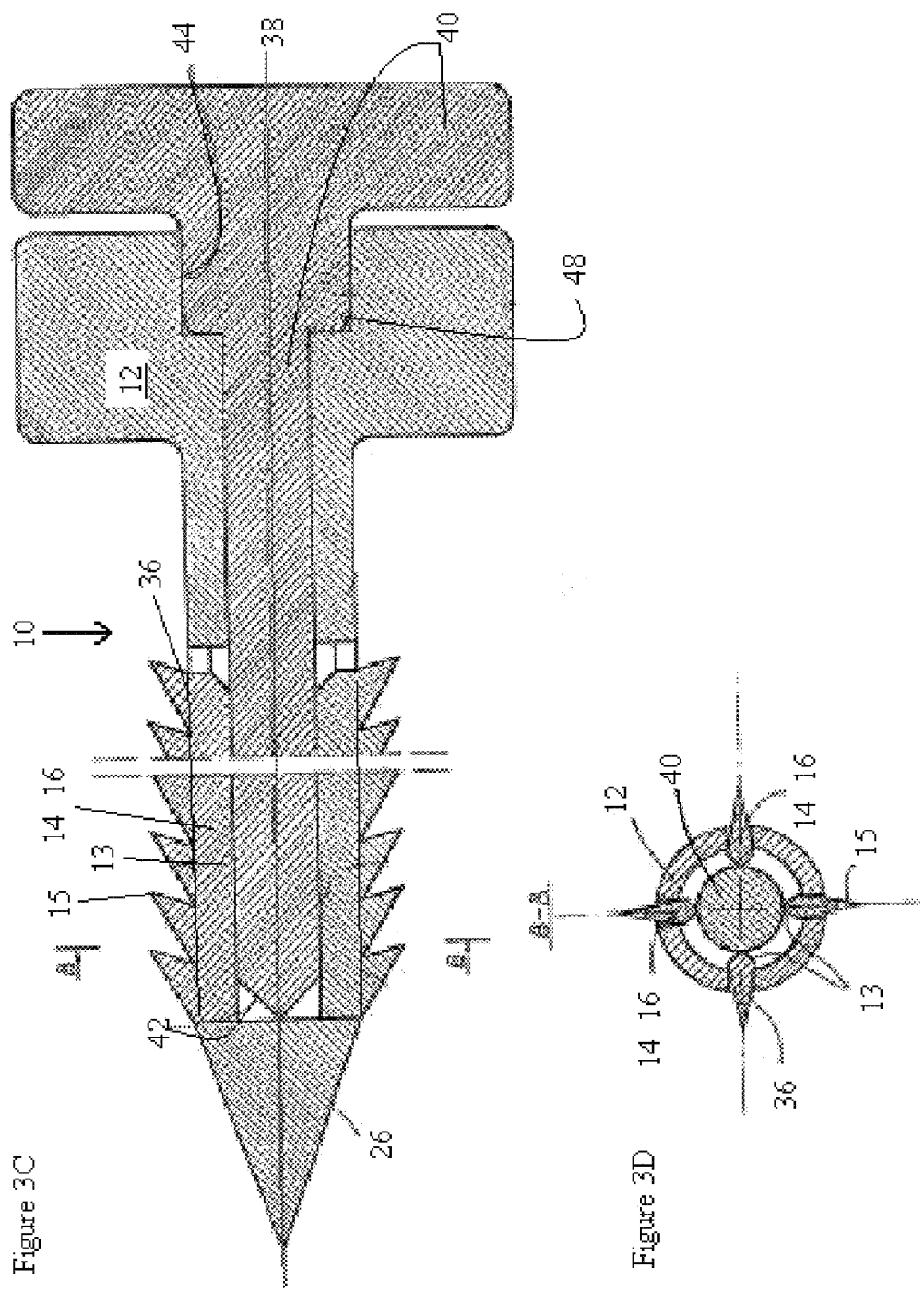

DEVICE AND METHOD FOR TREATING VARICOSE VEINS

RELATED APPLICATIONS

This application is a divisional of U.S. patent application Ser. No. 11/579,927 filed on Nov. 8, 2006, which is a National Phase of PCT Patent Application No. PCT/IL2005/000494 having International Filing Date of May 10, 2005, which claims the benefit of priority of Israel Patent Application No. 161928 filed on May 11, 2004, now Israel Patent No. 161928. The contents of the above Applications are all incorporated herein by reference.

FIELD AND BACKGROUND OF THE INVENTION

The present invention relates to devices for treating varicose veins in general, and in particular, to a surgical instrument for removing varicose veins.

Varicose veins are a condition of the superficial veins of the lower extremities in which one or more one-way valves within the veins have ceased to function efficiently, resulting in blood flow contrary to the normal direction of flow. This results in the build up of pressure inside portions of the vein, causing the veins to become abnormally twisted, distorted and prominent, yielding unsightly and often painful bulges on the lower extremities. Some 20% of women in the general population suffer from some degree of varicose veins. In some 5-7% of sufferers, an operation is required in order to remove the damaged veins, so as to permit blood flow through alternative routes. In others, cosmetic surgery and treatment are desired in order to remove the unsightly superficial varicose veins from the extremities.

The surgical instruments for removal of superficial varicose veins from lower extremities that can be found on the market today are relatively expensive, technically complex, complicated in use and require an incision through a skin layer over each superficial varicose vein or vein-knot (using the Winkling method) which is to be removed. The result can be ten to fifteen incisions during a single operation. These incisions result in the formation of many unattractive scars and, sometimes, in inflammation and infection.

One example of a conventional method and apparatus for removing varicose veins is described and claimed in U.S. Pat. No. 6,436,116 to Spitz et al. The method described in this patent includes making an incision through a skin layer of a patient, inserting a surgical instrument including a light source through the incision, visualizing the vein through the skin layer using the light source positioned subcutaneously and in proximity of the vein, and cutting the vein using the surgical instrument. The instrument further includes means for irrigating and tumescing a surgical region in proximity of the vein, and a vacuum source for aspirating cut venous tissue through the surgical instrument. This apparatus is very complicated, is complex to manufacture and maintain, and requires electricity to function.

A simpler apparatus is shown in U.S. Pat. No. 5,792,168. This apparatus is used to form an incision through the skin layer and engage a superficial vein for extraction of a segment of the vein through the incision. Once extracted, the exposed ends of the superficial vein may be ligated using known surgical techniques, and the ligated portions of the vein will return back through the incision. The apparatus of this patent includes a cylindrical shaft having a needle or scalpel at one end thereof for making an incision through the skin layer, and a cylindrical sleeve about the shaft arranged to slide relative to the needle. The facing surfaces of the needle and the cylindrical sleeve define a gripping region therebetween, and the gripping region can selectively engage the varicose vein to permit lifting of a selected portion of the vein out through the incision. This instrument also requires a separate incision above each vein to be treated.

Accordingly, there is a need for a surgical device for removing superficial varicose veins while requiring a relatively small number of incisions for effective treatment, and as a result improving cosmetic effects and reducing patient discomfort.

SUMMARY OF THE INVENTION

According to one aspect of the present invention there is provided a surgical instrument for treatment of superficial varicose veins in a body comprising at least one vein-engaging element disposed within or on a housing being adapted for insertion into a tissue (e.g. subcutaneous tissue), the at least one vein-engaging element being operable to a vein-engaging state whereby the at least one vein-engaging element protrudes from the housing at a length thereof.

According to further features in preferred embodiments of the invention described below, the housing is a hollow tube.

According to still further features in the described preferred embodiments the surgical instrument further comprises a substantially tapered tip located at an end of the housing, the tip being designed for allowing introduction of the surgical instrument into an incision through a skin layer.

According to still further features in the described preferred embodiments the surgical instrument further comprises a substantially pointed tip located at an end of the housing, the tip being designed for allowing introduction of the surgical instrument into an incision through a skin layer.

According to still further features in the described preferred embodiments the at least one vein-engaging element is a toothed vein-engaging element.

According to still further features in the described preferred embodiments the housing comprises at least one longitudinal slit for enabling the at least one vein engaging element disposed within the housing to protrude from the housing when in the vein engaging state.

According to still further features in the described preferred embodiments the at least one longitudinal slit is parallel to a longitudinal axis of the housing.

According to still further features in the described preferred embodiments the surgical instrument further comprises a state selector mechanism designed to operate the at least one vein-engaging element to a vein-engaging state.

According to still further features in the described preferred embodiments the state selector mechanism includes a plunger being insertable into the housing.

According to still further features in the described preferred embodiments the surgical instrument further comprising a locking element for locking the plunger when the vein-engaging element is in the vein-engaging state.

According to still further features in the described preferred embodiments the locking element includes a cylindrical collar about the plunger adapted and configured to frictionally engage a complementary depression in the hollow housing.

According to still further features in the described preferred embodiments the state selector mechanism includes at least one spring being for urging the at least one vein-engaging element to a vein-engaging state.

According to still further features in the described preferred embodiments the state selector mechanism includes an electrically activated servo mechanism for urging the at least one vein-engaging element to a vein-engaging state.

According to still further features in the described preferred embodiments the housing includes four longitudinal slits for enabling four toothed vein-engaging elements for selectively protruding through the slits, whereas the state selector mechanism is capable of simultaneously urging the four toothed vein-engaging elements to a vein-engaging state.

According to still further features in the described preferred embodiments the surgical instrument has a length of about 12 to 16 cm and a width of about 2 to 8 mm.

According to another aspect of the present invention there is provided a method of treating superficial varicose veins in a body region, the method comprising: (a) forming an incision in a skin layer adjacent to the body region; (b) inserting, through the incision a surgical instrument having a housing configured with at least one vein-engaging element being operable to a vein-engaging state whereby it protrudes from a length of the housing; (c) activating the at least one vein engaging element to the vein-engaging state; and (d) removing the surgical instrument, thereby treating the superficial varicose veins in the body region.

According to still further features in the described preferred embodiments steps (a)-(d) are repeated, thus forming an at least one additional incision, wherein the distance between two adjacent incisions along the same vein is greater than about 10 cm.

According to still further features in the described preferred embodiments step (b) is effected by inserting the surgical instrument into a varicose vein.

According to still further features in the described preferred embodiments step (c) is operable using a state selector forming a part of the surgical instrument.

According to still further features in the described preferred embodiments the housing is a hollow tube.

According to still further features in the described preferred embodiments the method further comprises a substantially pointed tip located at an end of the housing, the tip being designed for allowing introduction of the surgical instrument into an incision through a skin layer.

According to still further features in the described preferred embodiments the at least one vein-engaging element is a toothed vein-engaging element.

According to still further features in the described preferred embodiments the housing comprises at least one longitudinal slit for enabling the at least one vein engaging element disposed within the housing to protrude from the housing when in the vein engaging state.

The present invention successfully addresses the shortcomings of the presently known configurations by providing a surgical instrument which enables effective treatment of varicose veins through a small number of incisions and thus treatment therewith minimizes patient discomfort and scarring.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1M illustrate various embodiments of a surgical instrument for varicose vein treatment according to the teachings of the present invention.

FIGS. 2A-2B illustrate a side view of a surgical instrument constructed and operative in accordance with one embodiment of the present invention, in a non vein-engaging state (FIG. 2A), and in a vein-engaging state (FIG. 2B).

FIGS. 3A-3D illustrate a side sectional view (FIG. 3A) and a cross sectional view (FIG. 3B) of a surgical instrument constructed and operative in accordance with another embodiment of the present invention in an initial state prior to engaging a vein and at a vein-engaging state.

DESCRIPTION OF THE PREFERRED EMBODIMENTS

Figure 1E:
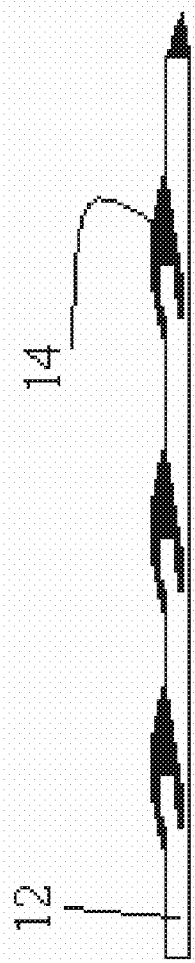

The present invention is of a surgical instrument/device and method for removing superficial varicose veins from a body, which instrument and method enable removal of several varicose veins through a single incision.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Devices for removing varicose veins are well known in the art, see for example U.S. Pat. No. 6,436,116 to Spitz et al. and U.S. Pat. No. 5,792,168 to Surval. In order to be effective, such devices require an operator to perform numerous incisions in order to treat varicose vein present in a body region targeted for treatment.

The present invention describes an instrument of a design which specifically addresses this limitation of prior art devices.

Thus, according to one aspect of the present invention there is provided a surgical instrument for treatment of superficial varicose veins in a body.

As used herein the phrase varicose veins refers to abnormally swollen or dilated veins.

As used herein the term "treating" when relating to varicose veins, refers to attenuating, or eliminating varicose veins, preferably superficial varicose veins of the legs.

The surgical instrument of the present invention includes at least one vein-engaging element disposed within or on a housing which is adapted for insertion into a tissue, such as subcutaneous tissue. As is further detailed hereinunder, the vein-engaging element is operable to a vein-engaging state whereby it protrudes from the housing at a length thereof.

Reference is now made to FIGS. 1A-1M, illustrating various embodiments of the surgical instrument of the present invention, which is referred to hereinunder as surgical instrument 10.

Surgical instrument 10 includes a housing 12 and at least one vein-engaging element 14 (three are shown in FIGS. 1A-B) which is disposed within or on housing 12 (on one or more sides). Preferably, surgical instrument 10 also includes a state selector mechanism 20 (also referred to hereinunder as mechanism 20) which is designed for urging vein engaging element 14 from a closed state to a deployed state (further described below).

Figure 1F:
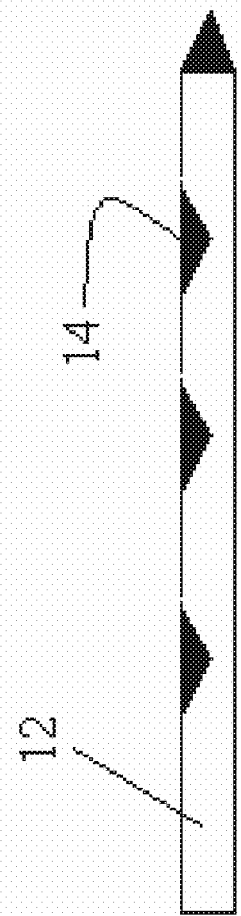
Figure 1G:
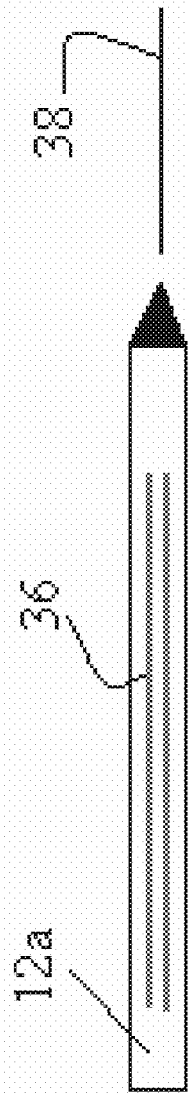

Housing 12 can be designed as an elongated member, which can be hollow or partially hollow for containing vein-engaging element(s) 14 within it (as shown in FIG. 1B). Housing 12 can be a flattened hollow housing 12b, like a knife with an extendable blade as shown in FIG. 1I, or a hollow tube 12b as shown in FIG. 1J, or any other desired design having an interior volume for containing at least one vein engaging-element 14 when in a non-deployed (closed) state. To enable deployment of vein engaging element 14, hollow housing 12 includes at least one opening that can be shaped as a circular hole or preferably a longitudinal slit 36 which is parallel to a longitudinal axis 38 of hollow housing 12 (as shown in FIG. 1G). Alternatively, housing 12 may also be a non-hollow, in which case vein-engaging elements 14 are positioned adjacent to and preferably flush with housing 12 (as shown in FIG. 1E). Preferably, housing 12 has a length (L) of about 12-16 cm (see FIGS. 1I-J), and a diameter/width (D), which varies from about 2 to 8 mm (depending on the dimensions of the varicose veins or vein-knots).

Housing 12 is preferably formed with a tapered tip 25 (as shown in FIG. 1I), or a pointed tip 26 (as shown in FIG. 1J) at a distal end 28 thereof (distal—with respect to an operator). Such a tip configuration enables non-traumatic introduction of surgical instrument 10 through an incision 30 made in skin layer 32 (as shown in FIGS. 1C-D). Tapered (25) or pointed (26) tips as well as housing 12 are preferably to fabricated from any appropriate bio-compatible material, including, for example, polymers or metals or any combination thereof.

Vein engaging element 14 is constructed from any suitable material (e.g., a biocompatible metal or polymer or a combination thereof), and is configured for engaging a vein 34 when in a vein-engaging state (deployed state). Vein-engaging element 14 can be a toothed vein-engaging element 16 (as shown in FIGS. 1K-L), or a hooked vein-engaging element 18 (as shown in FIG. 1M). In any case, the shape and size of vein engaging element 14 is selected so as to enable vein engagement when surgical instrument 10 is in operation. FIG. 1K illustrates a single toothed vein-engaging element 16 having a relatively wide base 13, narrowing to a sharp pointed tooth 15 at the outer edge. Furthermore, tooth 15 may have any desired shape as long as it slopes towards proximal end 24 of surgical instrument 10 (towards an operator). Sharp pointed tooth 15 must slope towards proximal end 24, for puncturing, engaging and removing or tearing a wall of vein 34 while surgical instrument 10 is being removed (pulled out) from the tissue of the patient. FIG. 1L illustrates a toothed vein-engaging element 16 having a plurality of sharp pointed teeth 15. Using plurality of sharp pointed teeth 15 in a toothed vein-engaging element 14 enables treatment of vein 34 more efficiently, since it increases the likelihood of vein engagement. FIG. 1M illustrates a hooked vein-engaging element 18 having the shape of a hook 19. According to this embodiment hook 19 catches onto vein 34 or its wall and when surgical instrument 10 is removed, hook 19 tears vein 34.

Figure 1H:
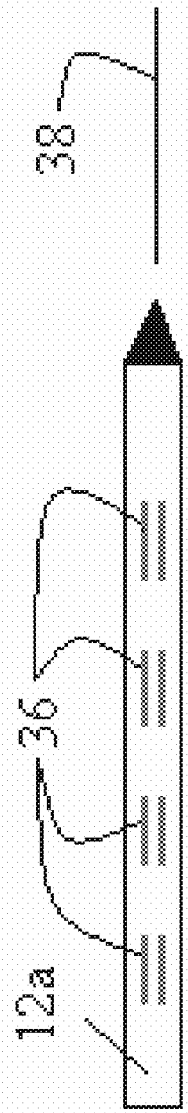

Vein engaging element 14 is operable from a closed state in which it is sequestered within housing 12 or flush against it (see FIGS. 1E-F) to a deployed state (vein engaging state—a state which enable element 14 to engage a vein), in which it protrudes from housing 12 (See FIG. 1A). FIGS. 1E and 1F illustrate two embodiments of vein-engaging element 14 placement. FIG. 1E illustrates surgical instrument 10 constructed such that vein engaging element 14 is placed on housing 12. FIG. 1F illustrates the surgical instrument 10 constructed such that the at least one vein engaging element 14 is placed within housing 12. In order to enable the latter embodiment, housing 12 is a hollow housing 12 (see FIGS. 1G-1J) having at least one longitudinal slit 36, which is parallel to a longitudinal axis 38 of the hollow housing 12. Preferably, one to four slits 36 are included, depending on the width/diameter of housing 12. Additionally, slits 36 are preferably located symmetrically about hollow housing 12. If desired, slits 36 may be continuous for the entire length of hollow housing 12 as shown in FIG. 1G, or constitute a plurality of shorter slits 36 spaced from one another forming broken lines along the length of hollow housing 12 as shown in FIG. 1H, to increase the housing's stiffness and strength.

State selecting mechanism 20 (also referred to herein as mechanism 20) is disposed within or on housing 12. Mechanism 20 is configured to be easily operated by an operator. Any one of several state selector mechanisms 20 can be utilized by surgical instrument 10. For example, springs, levers or cams which are disposed within or on housing 12, or a hydraulic mechanism (syringe-like) which is disposed within housing 12 can be utilized to activate deployment of vein engaging element 14. Such activation can be effected via twisting, pushing, pulling and the like. Alternatively, a simple electronic circuit which includes a power supply, switch and servo can be utilized for such purposes. One of ordinary skill in the art would be more than capable of designing and deploying various embodiments of state selector mechanism 20.

One embodiment of mechanism 20, illustrated in FIGS. 2A-B, is a plunger 40 which is suitable for use by a hollow housing 12 embodiment of surgical instrument 10. Plunger 40 is sized for insertion into hollow housing 12. FIG. 2A illustrates surgical instrument 10 with the plunger 40 prior to activation of a vein-engaging state. Pushing plunger 40 between vein-engaging elements 14 causes sharp pointed teeth 15 of vein-engaging elements 14 to protrude through slits 36 (FIGS. 3C-3D), until wide base 13 is stopped by the edges of slits 36. Preferably, plunger 40 has a cone-shaped tip 42, which makes it easier to insert between the ends of the vein engaging elements 14, separate them, and urge them to slide towards their respective slits 36. Alternatively, vein engaging elements 14 can be coupled to one another or formed as a single expandable unit.

Preferably, a locking mechanism 44 is provided to lock plunger 40 in place in hollow housing 12 in the vein-engaging state of FIGS. 3C-3D. In the illustrated embodiment (FIGS. 3A-D), locking mechanism 44 includes a cylindrical collar 46 which is adapted and configured to seat in and frictionally engage a mating depression 48 within hollow housing 12. Alternatively, any other suitable locking mechanism can be employed to permit a surgeon to lock surgical instrument 10 in the vein-engaging state for ease of removal of surgical instrument 10 and the vein pieces from the tissue of a patient.

FIGS. 3A-3D illustrate a side sectional view and a cross sectional view of surgical instrument 10 constructed and operative in accordance with one embodiment of the present invention in an initial state prior to being in a vein-engaging state. In the embodiment described herein, the state selecting mechanism 20 is the plunger illustrated in FIGS. 2A-2B herein above. Surgical instrument 10 includes a tube shaped hollow housing 12, and further includes four longitudinal slits 36 which are parallel to longitudinal axis 38 of hollow housing 12. Furthermore, in this embodiment, slits 36 are located symmetrically about hollow tube housing 12. Additionally, four toothed vein-engaging elements 16 are disposed within hollow housing 12. Furthermore, toothed vein-engaging elements 16 are adapted and configured to selectively partially protrude through longitudinal slits 36. Moreover, a configuration of vein-engaging elements 16 disposed around (e.g., following a radial pattern) the tube shaped hollow housing 12 is preferred, in order to permit the tearing and/or removal of more than one vein 34 at a time.

It will be appreciated that the thickness of the vein-engaging elements and the length of the teeth thereon depend on the diameter of hollow housing 12. When the instrument is assembled and ready for use, before insertion of the plunger, the teeth of vein-engaging elements 16 are hidden inside housing 12. Since the teeth slope away from the tip of the instrument, even if they protrude slightly prior to deployment, they will be pushed back inside the tube as long as the instrument is being inserted into the body. Once the instrument is in place, and the plunger has been inserted to the end of the tube, the teeth preferably protrude about 0.5 to 1 mm from the slits. It will further be appreciated that the length and width of longitudinal slits 36 must be sized to ensure a tight fit of wide base 13 of vein-engaging elements 14, so that vein-engaging elements 14 cannot fall out of housing 12 through slits 36 during use.

In the above described embodiment, vein-engaging elements 14 are not coupled to one another, but rather support one another inside the tube shaped hollow housing 12. Additionally, plunger 40 is arranged to slide between wide bases 13 of vein-engaging elements 14 and urge them apart from one another and outwards towards slits 36 of housing 12.

Figure 4:
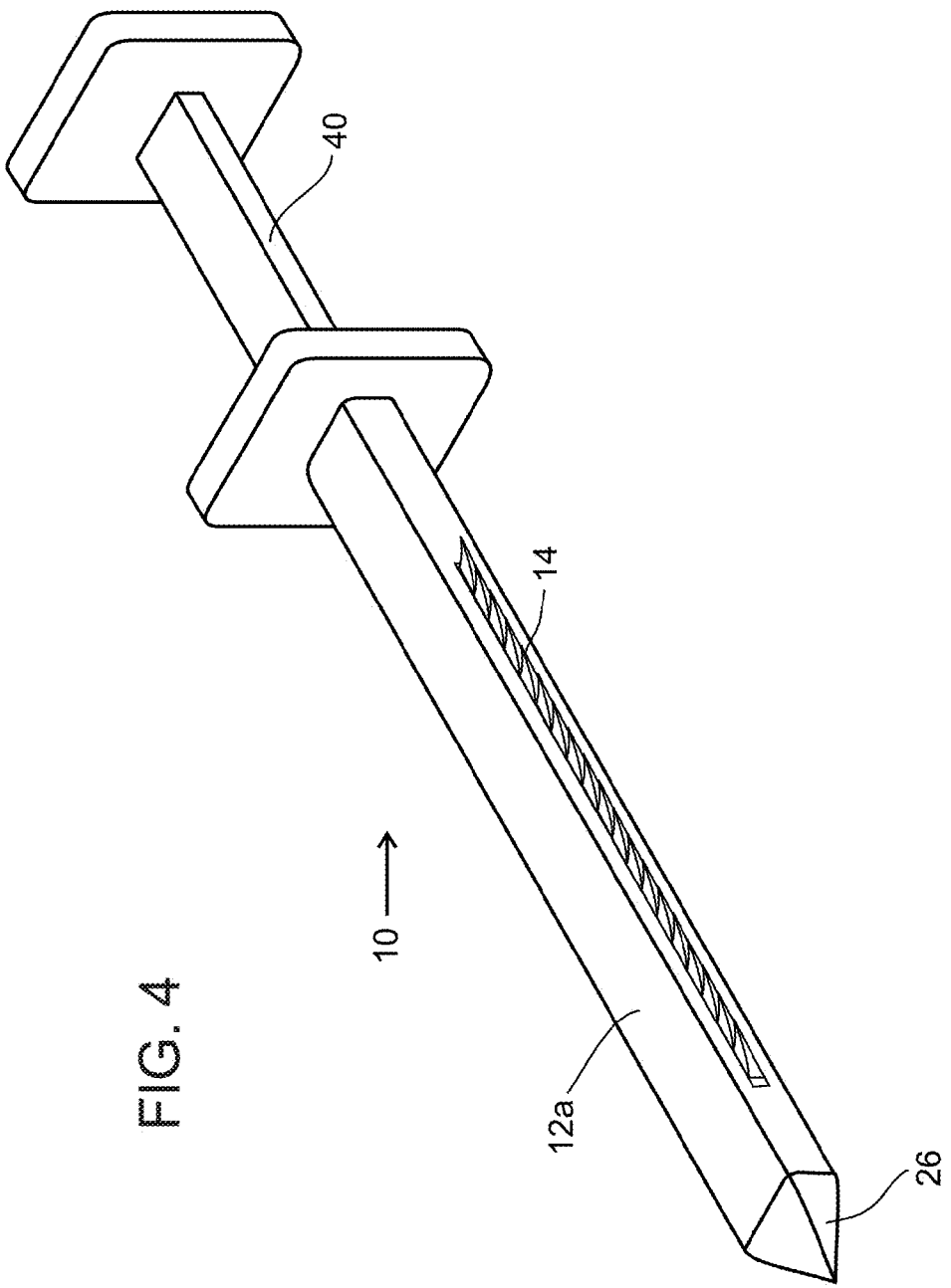
FIG. 4 illustrates a perspective view of a surgical instrument constructed and operative in accordance with another embodiment of the present invention.

Reference is now made to FIG. 4 illustrating a perspective view of a surgical instrument 10 constructed and operative in accordance with another embodiment of the present invention. In the embodiment described herein, the state selecting mechanism 20 is the plunger 40 as described in FIGS. 3A-3D herein above. In this embodiment, the housing 12 is a flattened housing 12a, similar to a knife having an extendable blade. One or two vein-engaging elements 14 are disposed within housing 12a, as is a plunger 40 for urging the at least one vein-engaging element 14 outwards to the vein-engaging state.

Figure 5:
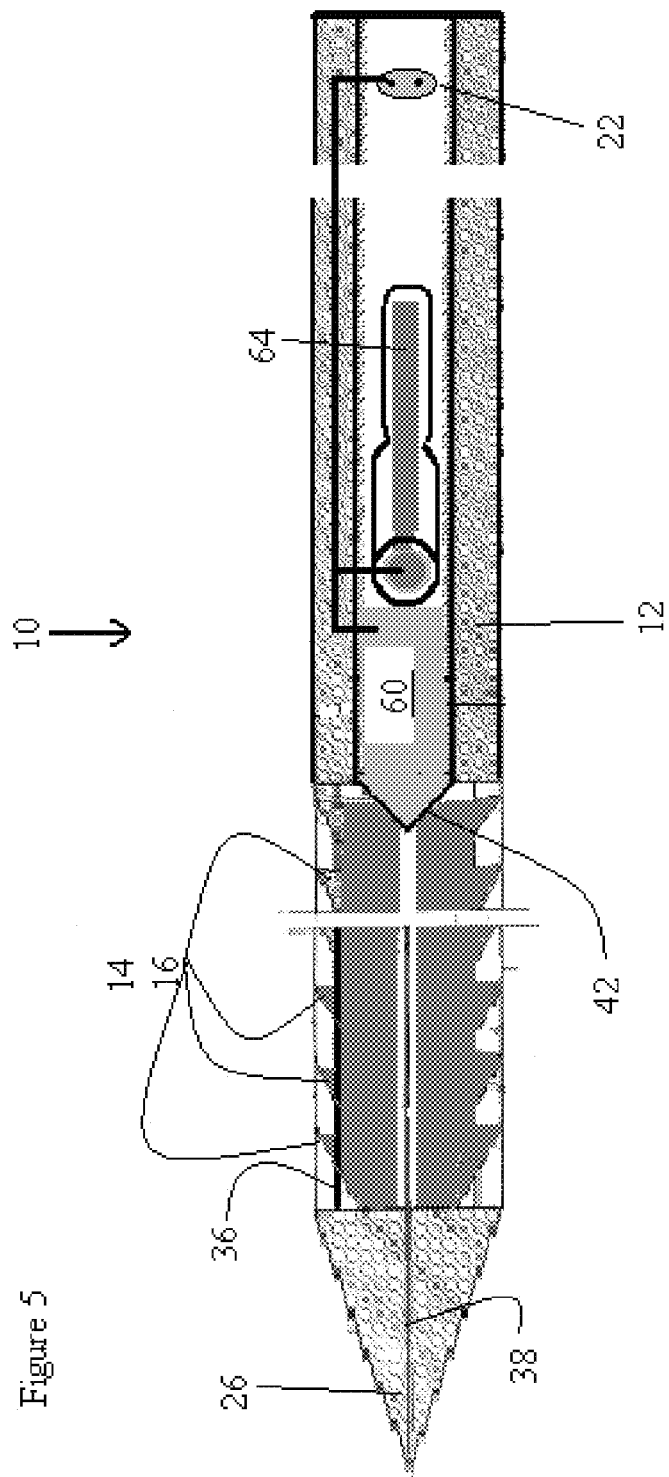
FIG. 5 illustrates a side sectional view of a surgical instrument constructed and operative in accordance to an additional embodiment of the present invention in an initial state prior to being in a vein-engaging state.

Reference is now made to FIG. 5 illustrating a side sectional view of a surgical instrument 10 constructed and operative in accordance with an additional embodiment of the present invention in an initial state prior to being in a vein-engaging state. In the embodiment described herein, the state selecting mechanism 20 includes a switch and a pushing element 60 having a conical tip 42 as in the case of the plunger 40 described in FIGS. 2A-B. Pushing element 60 is for urging the at least one vein-engaging element 14 to protrude through the at least one longitudinal slit 36 to a vein-engaging state (as was described for the plunger 40 in the previous embodiments herein above). Pushing element 60 is advanced forward by releasing at least one spring 64 disposed within housing 12 by activating the switch of state selector 22. Additionally, state selector 22 can have an option of fixing pushing element 60 in the vein-engaging state after the release of spring 64.

Figure 6:
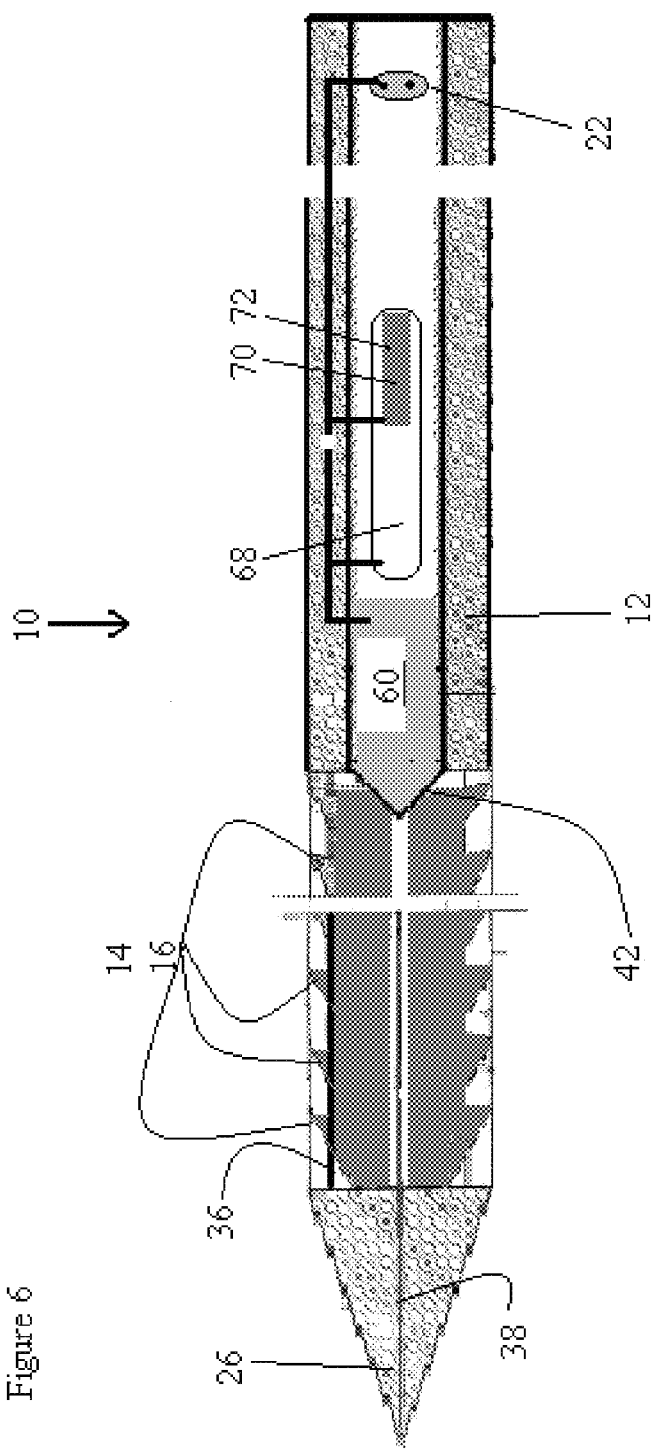
FIG. 6 illustrates a side sectional view of a surgical instrument constructed and operative in accordance with yet another embodiment of the present invention in an initial state prior to being in a vein-engaging state.

Reference is now made to FIG. 6 illustrating a side sectional view of a surgical instrument 10 constructed and operative in accordance with yet another embodiment of the present invention in an initial state prior to being in a vein-engaging state. In the embodiment described herein, state selecting mechanism 20 comprises a pushing element 60 having a conical tip 42 as in the case of the spring described in FIG. 5. Pushing element 60 is for urging vein-engaging element 14 to protrude through longitudinal slit 36 to a vein-engaging state (as was described in the previous embodiments herein above). According to this embodiment, pushing element 60 is advanced forward by activating an electrical circuit 68 disposed within housing 12. A power source 70 (e.g., a battery) is disposed within housing 12 for enabling the activation of the electrical circuit 68. Furthermore, state selector 22 is used for activating the electrical circuit, thus advancing pushing element 60 to a vein-engaging state. Additionally state selector 22 can have an option of fixing pushing element 60 in the vein-engaging state after activating electrical circuit 68.

As is mentioned hereinabove, surgical instrument 10 is utilized to treat varicose veins.

FIGS. 1C and 1D illustrate use of one embodiment of surgical instrument 10. In FIG. 1C surgical instrument 10 is inserted into and through vein 34 to be treated prior to being in a vein-engaging state. Surgical instrument 10 is then activated to a vein-engaging state and pulled back, thus tearing vein 34. It will be appreciated that although such intra-vein insertion may be unintentional, surgical instrument 10 can still be utilized to tear vein 34 whereas prior art devices, such as that described in U.S. Pat. No. 5,792,168, would be incapable of such functionality.

In FIG. 1D surgical instrument 10 is inserted into the body and along vein 34 to be treated prior to being in a vein-engaging state. Surgical instrument 10 is then activated to a vein-engaging state and pulled back, thus tearing vein 34.

FIG. 2B illustrates use of surgical instrument 10 which includes plunger 40 as mechanism 20. Pressing plunger 40 causes vein-engaging elements 16 to protrude through longitudinal slit 36, for example, about 0.5 mm, and hook into or tear the wall of the adjacent varicose vein 34 or vein knot 34. Preferably, plunger 40 is locked in this state, for ease of continued operation. Surgical instrument 10 can be removed now from the incision 30. As surgical instrument 10 is removed, toothed vein-engaging elements 16 may be pulled against, and hook onto or pass through, additional varicose veins 34 or vein knots 34. Surgical instrument 10 may be rotated about its longitudinal axis 38 while adjacent to treated vein 34, before or while the surgical instrument 10 is removed through the incision 30. The damaged vein portions which are hooked on vein-engaging elements 14, will be torn, and possibly pulled free from the body of the patient. If surgical instrument 10 is disposable, it may now be disposed of together with any removed vein portions. It will be appreciated that, in many cases, it is sufficient to tear the wall of the varicose vein 34, in order for it to cease functioning in a pathogenic manner (i.e. varicose state). The bleeding usually stops without assistance or by applying momentary pressure on incisions 30, and big subcutaneous hematomas are highly unusual. In the few cases where it is required, pressure can be applied or the vein ends can be tied, as is well known in the art.

This procedure is now repeated on subsequent veins 34 and vein-knots 34 preferably using new surgical instrument 10 that is introduced into the same incision 30. It will be appreciated that surgical instrument 10 can be pivoted to any direction required in an incision 30, in order to engage the desired vein. Thus, by using one incision 30 and sequentially introducing one or more instruments from different directions (any direction around the incision), the surgeon can remove all problematic veins within a radius approximately equal to the working length, L, of the surgical instrument 10, for example, 12-16 cm. It will further be appreciated that the use of a single incision to remove multiple varicose veins substantially reduces hematoma in the area following surgery.

If necessary, one or two additional incisions may be made in other areas having a vein or several veins to be removed, and the above procedure is repeated. In this fashion, by using the surgical instrument of the present invention, maximal clinical treatment and cosmetic effect can be achieved using only 2-3 small incisions. It will be appreciated that this is significantly fewer incisions than are typically required in a conventional operation. The Examples section below provides results obtained using the surgical instrument of the present invention. As is shown therein, the surgical instrument of the present invention is highly efficient in treating varicose veins.

It is a particular feature of the present invention that a plurality of veins can be removed or torn through a single incision, unlike using conventional techniques. This has several advantages. First, the possibility of infection is greatly reduced. Second, fewer incisions cause less trauma to the area. Third, the number of scars is significantly reduced as compared to prior art devices and techniques, thereby providing the desired cosmetic effect and effective treatment with fewer complications, while leaving the extremities much more attractive looking.

It will be appreciated that the surgical instrument of the present invention can also be used in cases where treatment is not immediately prescribed and yet cosmetic benefits can be gained.

As used herein, the term "about" denoted +/−10%.

While the invention has been described with respect to a limited number of embodiments, it will be appreciated that many variations, modifications and other applications of the invention may be made. It will further be appreciated that the invention is not limited to what has been described hereinabove merely by way of example. Rather, the invention is limited solely by the claims which follow.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions; illustrate the invention in a non limiting fashion. Two clinical trials using the surgical instrument for varicose vein treatment are described herein below; the first trial relates to usage of the surgical instrument in cadavers and the second for the usage in patients.

Example 1

Using the surgical instrument of the present invention, the present inventors performed a trial procedure on 30 lower body limbs of 15 cadavers (Table 1 below).

TABLE 1

| Limb No. | Age of deceased | Gender | Limb (Right/Left) | Number of Incisions | Incision Length |
|---|---|---|---|---|---|
| 1 | 70 | F | R & L | 3 | 5 mm |
| 2 | 43 | M | R & L | 3 | 5 mm |
| 3 | 48 | M | R & L | 3 | 5 mm |
| 4 | 84 | M | R & L | 3 | 5 mm |
| 5 | 84 | F | R & L | 4 | 5 mm |
| 6 | 58 | M | R & L | 4 | 5 mm |
| 7 | 56 | M | R & L | 4 | 5 mm |
| 8 | 74 | F | R & L | 2 | 5 mm |
| 9 | 54 | M | R & L | 4 | 5 mm |
| 10 | 48 | M | R & L | 4 | 5 mm |
| 11 | 34 | M | R & L | 4 | 5 mm |
| 12 | 54 | M | R & L | 4 | 5 mm |
| 13 | 50 | M | R & L | 4 | 5 mm |
| 14 | Age not known | F | R & L | 4 | 5 mm |
| 15 | 52 | F | R & L | 4 | 5 mm |

As is outlined in Table 1 above, the age of the deceased ranged between 34-84 years old, and the trial group included 10 males and 5 females. The surgical instrument used in this trial had a diameter of 4 mm, and thus the incisions made in the skin layer where 5 mm long. Furthermore, the incisions were made in skin regions suspected of being adjacent to veins. Extended varicose veins where observed in 5 of the cadavers.

In all cases were varicose veins were identified they veins were successfully engaged and torn, and removal of the surgical instrument indicated that no tissue other to than vein and subcutaneous adipose tissue were substantially damaged by the instrument (no remains of muscle or nerve tissue were observed on the instrument).

The results of this trial illustrated that the surgical instrument of the present invention can be successfully used in human tissue and that the vein engaging elements of the surgical instrument as well as their placement on the housing of the instrument enable highly effective grasping and tearing of varicose veins even in cases where such veins are extended and entangled.

In addition, the above described trial also illustrated that:

(i) the surgical instrument of the present invention can be used for treating varicose veins having a small diameter of about 1 mm;

(ii) use of the surgical instrument of the present invention enables complete removal of all varicose veins through 2-4 incisions only; and (iii) in configurations having one or two vein-engaging elements and a pointed tip, there is no need for performing incisions, since the pointed tip of the surgical instrument can be used for penetrating the skin; in such cases there will be no need for stitches following removal of the surgical instrument.

Example 2

The trial procedure described above was repeated on a group of patients. The purpose of this trial was to examine the use of the surgical instrument when applied for removal of varicose veins in a living human tissue. The operations where carried out on 5 lower body limbs of 4 patients (see Table 2 below). The age of the patients operated on ranged between 29-60 years old, and the sampling group included one male and 3 females. All females where post partum, one of which was operated on both legs. Four operations took place under general anesthesia while only was performed using epidural. All patients required standard superficial varicose vein removal, which includes performing incisions in the groin area and the leg. In two of the cases, two incisions were required while for the other three cases three incisions where required. The procedure took between 5 and 10 minutes to complete and in all cases there were no internal bleeding observed and no hematomas were formed. External bleeding was stopped using applied pressure for 1-3 minutes. In five surgical procedures a total of 13 incisions where made, of which only 9 required stitching. Following surgery, all patients were immediately bandaged with standard elastic bandages and re-bandged the following day. During the first twelve weeks following surgery, pain-relief medication was prescribed (non-narcotic analgesic) and none of the patients complained of strong pain which could be indicative of under-skin hematomas or nerve damage. This was probably due to the small number of incisions and therefore reduced damage to the tissue. During a 7-10 day recovery period no complications were observed and all of the patients returned to normal life including work.

TABLE 2

| No. | Age | Gender | Limb (Right/ Left) | Number of Incisions | Anesthesia | Complications |
| --- | --- | --- | --- | --- | --- | --- |
| 1 | 60 | M | R | 2 | general | None |
| 2* | 29 | F | R | 3 | general | None |
|  |  |  | L | 2 | general | None |
| 3 | 48 | F | L | 3 | general | None |
| 4 | 54 | F | R | 3 | epidural | None |

*operated on both legs

The clinical trial described above conclusively shows that the surgical instrument is highly effective for varicose vein treatment procedures in that it has shown to have positive affects both from the cosmetic point of view and from the clinical point of view.

It is appreciated that certain features of the invention, which are, for clarity, described in the context of separate embodiments, may also be provided in combination in a single embodiment. Conversely, various features of the invention, to which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A surgical instrument adapted to engage superficial varicose veins in a body from outside of the veins, comprising:
    a handle;
    an elongated housing attached to the handle; and
    an elongated vein-engaging element disposed within the housing, the vein-engaging element comprising a plurality of teeth arranged along a length of the vein-engaging element;
    said elongated vein-engaging element being operable to a vein-engaging state in which said plurality of teeth protrude from said housing along most of a length of said housing,
    wherein said housing includes at least one longitudinal slit in a wall of the housing, said slit disposed along most of a length of said housing, said slit configured to allow said at least one vein-engaging element to assume said vein-engaging state.

2. The surgical instrument according to claim 1, further comprising a state selector mechanism configured to press against said at least one vein-engaging element, thereby causing said at least one vein-engaging element to assume said vein-engaging state, and further comprising a locking mechanism for locking said surgical instrument in the vein-engaging state.

3. The surgical instrument according to claim 2, wherein said state selector mechanism includes an electrically powered mechanism for urging said at least one vein-engaging element to said vein-engaging state.

4. The surgical instrument according to claim 1, wherein at least a portion of said housing comprises a hollow tube and said at least one vein-engaging element is configured to be located within said hollow tube prior to assuming said vein-engaging state.

5. The surgical instrument according to claim 1, wherein said at least one vein-engaging element is configured to provide at least one of:
    a) puncturing a vein;
    b) engaging a vein;
    c) tearing at least a portion of a vein;
    d) ensnaring at least a portion of a vein;
    e) wrapping at least a portion of a vein around said housing while rotating said housing along a longitudinal axis of said housing; and
    f) severing a first portion of a vein from a second portion of a vein.

6. The surgical instrument according to claim 1, wherein said slit disposed along most of a length of said housing comprises said slit disposed along substantially an entire length of said housing.

7. A surgical instrument for treatment of superficial varicose veins in a body comprising:
    a pointed tip at a distal end of the surgical instrument, configured to be inserted into a tissue; and
    at least one sharp vein-engaging element comprising a plurality of teeth disposed along a housing being adapted for insertion into the tissue, whereby each of said at least one vein-engaging element protrudes from said housing along most of a length of said housing, each of said plurality of teeth being configured to engage the outside of at least one vein located in the tissue and being long enough to penetrate the wall of the vein,
    wherein said housing comprises at least one longitudinal slit in a wall of the housing, said slit disposed along most of a length of said housing. said slit configured a low said plurality of teeth to protrude from said housing said substantially entire length of said housing.

8. The surgical instrument according to claim 7, wherein said at least one vein-engaging element comprises a plurality of vein engaging elements disposed substantially along the entire length of said housing.

9. The surgical instrument according to claim 7, wherein said at least one vein-engaging element comprises a plurality of sharp vein engaging elements, each of said plurality of vein engaging elements radially disposed around said housing.

10. The surgical instrument according to claim 7, wherein said at least one vein-engaging element is comprises at least one of:
  a toothed vein engaging element; and
  a hooked vein engaging element.

11. The surgical instrument according to claim 7, wherein at least a portion of said housing comprises a hollow tube and said at least one vein-engaging element is configured to be located within said hollow tube prior to assuming said vein-engaging state.

12. The surgical instrument according to claim 7, including at least one plurality of vein-engaging elements and at least two of said at least one plurality of vein-engaging elements are substantially rigidly coupled to one another.

13. The surgical instrument according to claim 7, wherein said housing is rigid enough to stay straight relative to a longitudinal axis of the surgical instrument while pivoting to any direction required relative to an incision as a pivoting point, and a portion of said rigid housing is configured to be manipulated by an operator.

14. The surgical instrument according to claim 7, each of said at least one vein-engaging element being operable to a non-deployed state whereby each of said at least one vein-engaging element is disposed entirely within said housing.

15. The surgical instrument according to claim 7, wherein each of said at least one vein-engaging element is operable to a vein-engaging state.

16. The surgical instrument according to claim 7, wherein said slit disposed along most of a length of said housing comprises said slit disposed along substantially an entire length of said housing.

* * * * *